United States Patent [19]

Allison et al.

[11] Patent Number: 5,214,036
[45] Date of Patent: May 25, 1993

[54] BENZOPORPHYRIN DERIVATIVES FOR PHOTODYNAMIC THERAPY

[75] Inventors: Beth A. Allison; Anna M. Richter; P. Haydn Pritchard; Julia G. Levy, all of Vancouver, Canada

[73] Assignee: University of British Columbia, British Columbia, Canada

[21] Appl. No.: 491,674

[22] Filed: Mar. 8, 1990

[51] Int. Cl.[5] .................... A61K 31/40; A61K 47/42
[52] U.S. Cl. .................... 514/185; 514/410; 530/359
[58] Field of Search ............ 514/21.185, 410; 424/450; 530/359

[56] References Cited

U.S. PATENT DOCUMENTS

| 4,797,392 | 1/1989 | Chernomorsky | 514/185 |
| 4,849,207 | 7/1989 | Sakata et al. | 514/185 |
| 4,920,143 | 4/1990 | Levy et al. | 514/410 |

OTHER PUBLICATIONS

Horrobin, Chemical Abstracts, v. 106, 1987 Abstract 182699x.
Richter, et al., Proc. of SPIE, The Int. Soc. for Optical Engineering 997:132–138.
Kessel, (1977) *Biochem. Soc. Trans.* 5:139–140.
Lipson et al., (1961) *J. Natl. Cancer Inst.* 26 (1):1–11.
Richter et al., (1987) *J. Natl. Cancer Inst.* 79:1327–1332.
Mew et al., (1983) *J. Immunol.* 130:1473–1477.
Reyftmann et al., (1984) *Photochem. Photobiol.* 40:721–729.
Barel et al., (1986) *Cancer Letters* 32:145–150.
Kessel et al., (1989) *Photochem. Photobiol.* 49:579–582.
Figge et al., (1948) *Proc. Soc. Exptl. Biol. Med.* 68:640–641.
Zalar et al., (1977) *Arch. Dermatol.* 113:1392–1397.
Wooten et al., (1988) *Lasers in Surgery and Medicine* 8:294–300.
Rudel et al., (1974) *Biochem. J.* 139:89–95.
Havel et al., (1955) *J. Clin. Invest.* 34:1345–1353.
Kelley et al., (1986) *Methods in Enzymology* 128:170–181.
Jori et al., (1984) *Cancer Letters* 24:291–297.
Zhou et al., (1988) *Photochem. Photobiol.* 48(4):487–492.

Primary Examiner—Robert T. Bond
Assistant Examiner—E. C. Ward
Attorney, Agent, or Firm—Morrison & Foerster

[57] ABSTRACT

Green porphyrins (Gp), compounds important in photodynamic therapy, have been associated with lipocomplexes to reduce the required amount of photosensitizer through higher effective absorption and increased specificity. BPDs, especially in conjunction with the HDL fraction of plasma lipoproteins, has been shown to be particularly effective in this context. Pharmaceutical compositions in which these combinations are the active ingredients for use in diagnosis and treatment of tumors are also disclosed.

6 Claims, 8 Drawing Sheets

BENZOPORPHYRIN DERIVATIVES FOR PHOTODYNAMIC THERAPY

TECHNICAL FIELD

This invention relates generally to the treatment of tumors using the process of photodynamic therapy (PDT). In particular, the invention relates to methods of administering green porphyrins (Gp) in combination with plasma lipoproteins or liposomes ("lipocomplexes") so as to improve transport and delivery to tumors with enhanced cytotoxicity. The invention further relates to Gp-lipocomplex compositions for use in the aforementioned methods.

BACKGROUND ART

It has been known for some time that porphyrin related compounds accumulate at higher concentrations in tumor tissue as compared to normal tissue, and that irradiation of these compounds using light of the proper wavelength results in an energized form which, upon decay, results in cytotoxicity. These compounds have therefore been useful in PDT, a procedure for treating cancer that uses tumor-localizing photosensitizers.

The effectiveness of PDT is believed to be based on two toxic modes of action of photosensitizers. First, retained photosensitizers such as porphyrins cause localized necrosis of vascular tissue which in turn leads to cell death. The second mode of action involves exciting the photosensitizers by exposure to light. When porphyrins are exposed to light it is believed that singlet oxygen radicals are formed which directly damage cell walls leading to cell death. See, e.g., D. Kessel, *Biochem. Soc. Trans.* 5:139-40 (1977).

The use of porphyrin compounds in PDT has an unfortunate side effect—prolonged photosensitivity in the skin of treated patients persisting for several weeks. Efforts have been made in the art to reduce this side effect by minimizing the quantity of porphyrins required for PDT.

Hematoporphyrins, and hematoporphyrin derivatives (HPDs) are the primary porphyrin compounds used in PDT today. (See, e.g., "Porphyrin Photosensitization," Kessel, D. et al. eds. (1983 Plenum Press), R. L. Lipson et al., *J. Natl. Cancer Inst.* 26:1-8 (1961).) The maximum absorbance of hematoporphyrins and HPDs occurs at around 400 nm, but there is also absorbance around 630 nm, at a range where there is much scattering and absorbance by tissue. (See, e.g., A. M. Richter et al., *J. Natl. Cancer Inst.* 79:1327-32 (1987)).

Thus, one goal in the PDT field has been to find a suitable porphyrin derivative that has a maximum absorbance outside the range of tissue absorbance and scattering. One such class of porphyrins that is being studied is a set of modified porphyrins referred to as "green porphyrin" (also referred to as "Gp" herein) of which the hydro-monobenzoporphyrins ("BPDs") are a subclass. The disclosure of U.S. patent application Ser. No. 07/414,201, now U.S. Pat. No. 5,095,030, hereby incorporated by reference, discusses in detail the nature of Gp. The maximum absorbance of Gps are in the 670-780 nm range, where there is little tissue absorbance. The cytotoxicity of a BPD is discussed in A. M. Richter et al., *J. Natl. Cancer Inst.* 79:1327-32 (1987)

Another goal in PDT research has been to increase the specificity of the porphyrin compounds for the targeted tumor cells. Considerable advancements were made by conjugating hematoporphyrins to tumor-specific antibodies. In one case, for example, hematoporphyrin was covalently coupled to a monoclonal antibody directed to murine myosarcoma cells. D. Mew et al., *J. Immunol.* 130:1473-77 (1983).

A recent advancement in this direction is the discovery of the role of lipoproteins as carriers of porphyrins in serum. (See Reyftmann et al. *Photochem. Photobiol.* 40:721-29 (1984).) Lipoproteins have similarly been implicated in hematoporphyrin transport in Barel et al., *Cancer Letters* 32:145-50 (1986) and in BPD transport in Kessel et al., *Photochem. Photobiol.* 49:579-82 (1989).

Barel et al., supra, observed that formation of complexes of hematoporphyrin and low density lipoproteins (LDLs) led to more specific delivery to tumor tissue, although hematoporphyrin itself had a higher affinity for high density lipoproteins (HDLs). Similarly, Kessel et al., supra, observed that BPD compounds bound primarily to HDLs over other lipoprotein fractions.

The present invention is directed to the aforementioned problems and goals. The inventors herein have now discovered that precomplexation of certain BPDs with lipoprotein fractions results in increased specific delivery of photosensitizers to tumor cells. The amount of photosensitizer required for effective treatment is thereby reduced both by: (1) decreased absorbance of light at the drug absorption wavelength by the surrounding tissue; and (2) by increased specific delivery of the drug to tumor cells.

DESCRIPTION OF THE PRIOR ART

Background References. Figge et al., *Proc. Soc. Exctl. Biol. Med.* 68:640-41 (1948) presents an account of porphyrin accumulation in tumor tissue. D. Kessel et al. eds., "Porphyrin Photosensitization" (1983: Plenum Press) presents the use of photosensitizers such as porphyrins combined with irradiation to effect the destruction of malignant cells. G. L. Zalar et al., *Arch. Dermatol.* 113:1392-97 (1977), and R. S. Wooten et al., *Lasers in Surgery and Medicine* 8:294-30 (1988) examine the phototoxicity of hematoporphyrin derivatives in particular following systemic administration.

Lipoproteins. The characterization of plasma lipoproteins has been effected using column chromatography by L. L. Rudel et al., *Biochem. J.* 139:89-95 (1974), and using ultracentrifugation by R. J. Havel et al., *J. Clin. Invest.* 34:1345-53 (1955), and J. K. Kelly et al., *Methods in Enzymology* 128:170-81 (1986). G. Jori et al., *Cancer Letters* 24:291-97 (1984) and A. Barel et al., *Cancer Letters* 32:145-50 (1986) examine the role of lipoprotein fractions in the transport of hematoporphyrins in vivo. C. Zhou et al., *Photochem. Photobiol.* 48:487-92 (1988) examines the ultrastructural cellular effect of PDT using porphyrins associated with lipoproteins.

Benzoporphyrin and Benzoporphyrin Derivatives (BPDs). A. M. Richter et al. *J. Natl. Cancer Inst.* 79:1327-32 (1987) performed preliminary studies on the phototoxicity of BPDs. (See also A. M. Richter et al., *Proceedings of SPIE—The International Society for Optical Engineering,* 997:132-38 (1988)) D. Kessel, *Photochem. Photobiol.* 49:579-82 (1989) examined in vitro photosensitization with a BPD. A. M. Richter et al., *J. Photochem. Photobiol.* 50 (in print 1990) studied the *in vivo* biodistribution of BPDs in normal and tumor-bearing mice.

SUMMARY OF THE INVENTION

It is accordingly a primary object of the present invention to overcome the disadvantages of the prior art, in particular the need to use an excessive amount of photosensitizer in PDT, resulting in a persistent skin photosensitivity associated therewith.

It is a further object of this invention to provide a composition for the treatment of tumors by PDT as above, wherein that composition includes a Gp that absorbs in a wavelength range where there is little tissue absorption or scattering.

It is another object of this invention to provide a composition for the treatment of tumors by PDT as above, wherein that composition includes a fraction of plasma lipoproteins that enhance the specific delivery of the Gp to tumor cells.

It is yet another object of this invention to provide a method for locating tumors in cancer patients by using Gp and a lipocomplex to achieve the advantages described above.

Additional objects, advantages and novel features of the invention will be set forth in part in the description which follows, and in part will become apparent to those skilled in the art upon examination of the following, or may be learned by practice of the invention.

In one aspect of the invention, a pharmaceutical composition is provided for the identification and treatment of targeted cells, wherein that composition contains a Gp and a lipoprotein mixture derived from human plasma. In a particularly preferred embodiment, the Gp is a BPD and the lipoprotein mixture consists essentially of HDLs.

In another aspect of the invention, a method is provided for impairing the metabolism or effecting the destruction of targeted cells or tissues, the method comprising administration of the above-described composition to a patient followed by light exposure.

In yet another aspect of the invention, a method is provided for identifying the location of tumors in cancer patients, the method comprising the administration of the above-described composition to a patient, followed by light exposure and monitoring of subsequent fluorescence.

DETAILED DESCRIPTION OF THE INVENTION

Definitions

A "pharmaceutically acceptable" solution as used herein refers to any carrier-type solution which is generally suitable for administration by injection. Injection may be either subcutaneously, intramuscularly or intravenously. These solutions can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

"Green porphyrin" ("Gp") refers to a set of modified photoactive porphyrins which, by virtue of their derivatization, undergo a shift in absorption maxima so that they appear green rather than red, indicating their absorption of wavelengths in the red-orange range. This collection of derivatives has therefore been nicknamed "green porphyrin" (Gp) and has been shown to confer sensitivity on target cells at concentrations greater than 10-fold lower than those required for hematoporphyrin (Hp) or HPD. These compounds are disclosed in copending U.S. Ser. No. 414,201, filed 28 Sep. 1989 and incorporated herein by reference.

Figure 1:
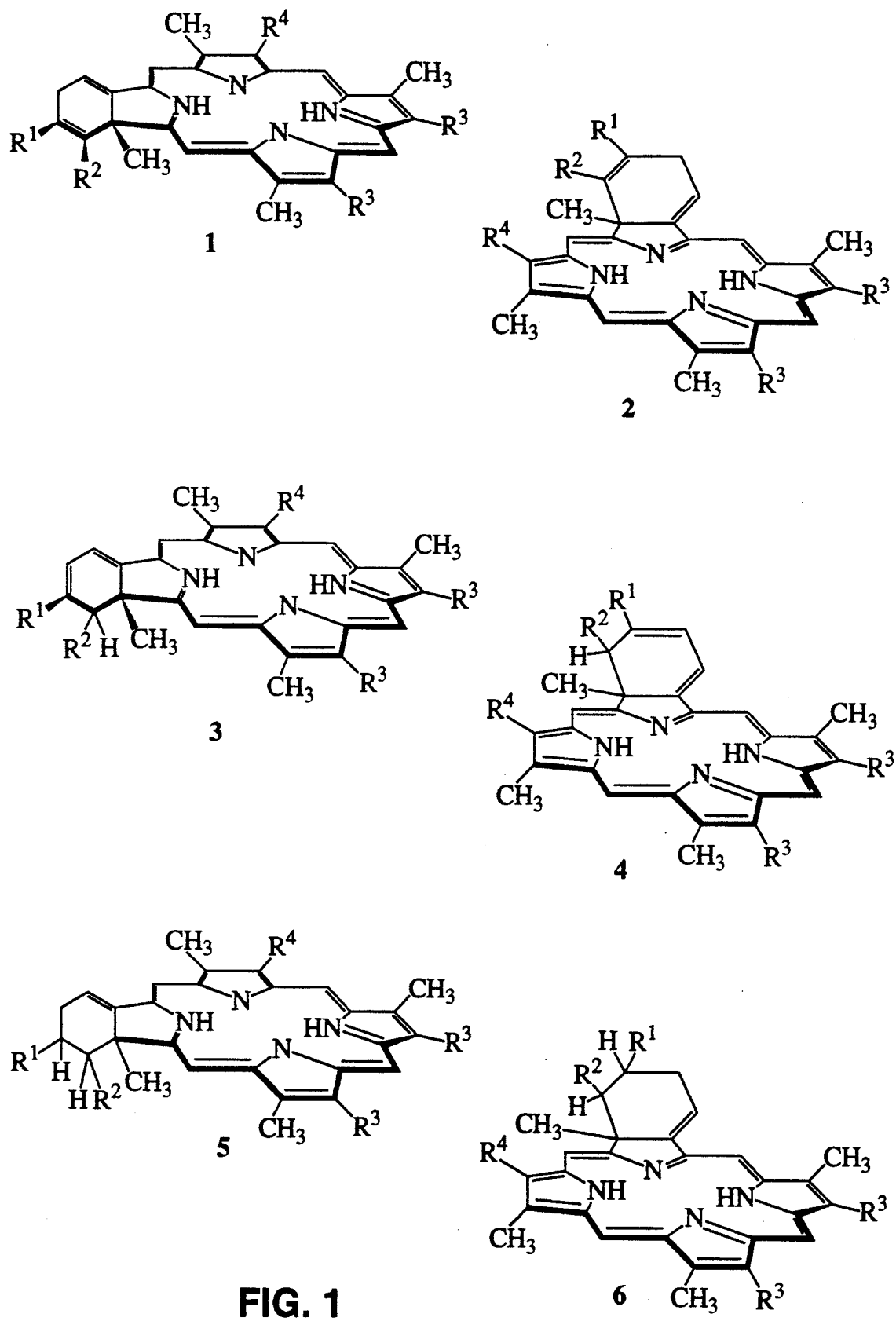
FIG. 1 shows the structure of green porphyrin (Gp) compounds used in the methods and conjugates of the invention.

The Gp is selected from a group of porphyrin derivatives which can be obtained using Diels-Alder reactions of acetylene derivatives with protoporphyrin under conditions which effect a reaction at only one of the two available conjugated, nonaromatic diene structures present in the protoporphyrin-IX ring system (rings A and B). The formulas shown in FIG. 1 represent the green porphyrins of the invention. Also, for convenience, an abbreviation of the term hydro-monobenzoporphyrin derivative—"BPD"—is generally used to refer to compounds of formulas 3 and 4 of FIG. 1 as these are the preferred forms of Gp. The substituents represented are further described below.

Dimeric and multimeric forms of Gp/porphyrin combinations can also be employed, providing additional absorption wavelengths and amplifying the ability of the Gp compound to absorb light on a per mole basis.

A "lipocomplex" as used herein refers to either a "lipoprotein mixture" as described below or to liposomes composed of phospholipid bilayers.

A "lipoprotein mixture" as used herein refers to a homogeneous, or more usually heterogeneous mixture of lipoproteins or lipoprotein fragments, essentially albumin-free, derived from human plasma. These lipoproteins may be separated from other plasma components by methods including, but not limited to, ultracentrifugation and column chromatography, and they may be naturally occurring or synthetic. Lipoproteins may also be lyophilized, and later reconstituted in a usable form. The lipoprotein mixture may also consist of lipoproteins incorporated in phospholipid bilayers.

"HDLs," "LDLs," and "VLDLs" refer to high density, low density, and very low density lipoproteins. These groupings refer to fractions of the above-defined lipoprotein mixture, isolated therefrom by separation techniques such as ultracentrifugation or column chromatography, and having a characteristic specific gravity range. Typically, HDLs have a specific gravity between about 1.06 and 1.21 g/ml; while LDLs have a specific gravity between about 1.02 and 1.06 g/ml, and VLDLs have a specific gravity less than about 1.02 g/ml.

"Liposomes" as used herein refer to spherical or elongated lipid bilayers that enclose an aqueous compartment. Liposomes may be multilamellar or unilamellar. They are more usually unilamellar and composed of major membrane lipids such as phosphatidyl choline, phosphatidyl ethanolamine, phosphatidyl serine and phosphatidyl glycerol.

The Composition

There are two active ingredients in the compositions of this invention: a Gp and a lipocomplex. Together, these components greatly reduce the amount of photosensitizer required for PDT in the prior art.

All of the compositions of the invention employ as the light absorbing compound a "green porphyrin"—a derivative of the protoporphyrin ring system which has a light absorption maximum in the range of 670-780 nanometers. FIG. 3 is the absorption spectrum of one of the compounds of the invention illustrated in FIG. 2, BPD-DA, wherein $R^1$ and $R^2$ are carbomethoxy, in comparison to HPD and Photofrin ® II compositions. Only BPD-DA has a major absorption peak at about 685 nm.

In general, this shift is achieved by effectively saturating one of the two $\pi$-bonds in one, but not two, of the four pyrrole rings which constitute the typical porphyrin system. In protoporphyrin-IX two of the pyrroles contain vinyl substitutions such that the exocyclic $\pi$-bond is conjugated to one of the two $\pi$-bonds in the ring. A Diels-Alder reaction involving one of these conjugated systems with an acetylene derivative dienophile results in a fused cyclohexadiene—referred to herein as "hydrobenzo"—fused to the A or B ring, as shown in formulas 1 and 2. Rearrangement of the $\pi$ system in the hexadiene ring results in the compounds of formulas 3 and 4; reduction provides compounds of formulas 5 and 6. All of these compounds provide the desired shift in absorption maximum.

Specific preparation of some compounds useful in the invention or their precursors is described by Morgan, A. R., et al, *J Chem Soc Chem Commun* (1984) pp. 1047-1048; and by Pangka, B. S. et al, *J Organic Chem* (1986) 51:1094. There are obtained directly from reaction of protoporphyrin with, for example dimethyl acetylene dicarboxylate (DMAD), compounds shown as formulas 1 and 2 of FIG. 1, wherein $R^1$ and $R^2$ represent the substituents on the original acetylene-derived Diels-Alder reagent, $R^1C\equiv CR^2$—in this case, carbomethoxy. $R^1$ and $R^2$ are, generally, specifically carbalkoxy groups such as carbomethoxy or carboethoxy. $R^3$ represents substituents present on the porphyrin used in the reaction or substituents derived therefrom. In the Morgan reference, the reaction substrate was protoporphyrin-IX dimethyl ester; thus the ligand $R^3$ was, in all cases, 2-carbomethoxyethyl.

In general, $R^1$ and $R^2$ are each, independently, moderate electron-withdrawing substituents, and are, most commonly, carbalkoxy, or alkyl or aryl sulfonyl, or any other activating substituents, which are not sufficiently electron-withdrawing to result in reaction with both A and B rings rather than reaction with only one, such as cyano or —CONR$^5$CO— wherein R$^5$ is aryl or alkyl. One of $R^1$ and $R^2$ may optionally be H while the other is an electron withdrawing substituent of sufficient strength to facilitate the Diels-Alder reaction.

As used herein, carboxy is, as conventionally defined, —COOH and carbalkoxy is —COOR, wherein R is alkyl; carboxyalkyl refers to the substituent —R'—COOH wherein R' is alkylene; carbalkoxyalkyl refers to —R'—COOR wherein R' and R are alkylene and alkyl respectively. Alkyl is a saturated straight or branched chain hydrocarbyl of 1-6 carbon atoms such as methyl, n-hexyl, 2-methylpentyl, t-butyl, r-propyl, and so forth. Lower alkyl as used herein refers to a straight or branched chain saturated hydrocarbon moiety having one to four carbon atoms. Alkylene is as alkyl except that the group is divalent. Aryl or alkyl sulfonyl moieties have the formula $SO_2R$ wherein R is alkyl as above-defined, or is aryl, wherein aryl is phenyl optionally substituted with 1-3 sutstituents independently selected from halo (fluoro, chloro, bromo or iodo), lower alkyl (1-4 C) or lower alkoxy (1-4 C). In addition, one or both $R^1$ of $R^2$ can itself be aryl—i.e., phenyl optionally substituted as above-defined.

As shown in FIG. 1, the adduct formed by the reaction of $R^1$—$C\equiv C$—$R^2$ with the protoporphyrin-IX ring system ($R^3$ is a protected form of 2-carboxyethyl such as 2-carbomethoxyethyl or 2-carboethoxyethyl; $R^4$ is $CH=CH_2$) are compounds of the formulas 1 and 2 wherein the compound in formula 1 results from addition to the A ring and formula 2 results from addition to the B ring. In these resulting products of formulas 1 and 2, $R^4$ remains $CH=CH_2$, however this vinyl group is readily derivatized to other embodiments of $R^4$ by addition to or oxidation of the vinyl ring substituent of ring B in formula 1 or ring A in formula 2. The addition or oxidation products can be further substituted if the added substituents are functional leaving groups—for example —Br may be substituted by —OH, —OR (R is alkyl 1-6 C as above), or —NH$_2$, —NHR, —NR$_2$, etc. In preferred embodiments, one of the added substituents is hydrogen, and the other is selected from the group consisting of halo (fluoro, chloro, bromo or iodo), hydroxy, lower alkoxy, amino or an amide, sulfhydryl or an organo-sulfide or can be, itself, hydrogen. Addition to the vinyl group does not appreciably change the absorption spectrum of the resulting compound. The product of the Markovnikov addition of water provides a substituent structure analogous to the hematoporphyrin ring system at the relevant ring. Thus, the compounds of the invention include various groups as $R^4$, including substituents which provide additional porphyrin or porphyrin-related ring systems, as will be further described below.

$R^3$ in protoporphyrin-IX is 2-carboxyethyl (—CH$_2$CH$_2$COOH). However, the nature of $R^3$ (unless it contains a $\pi$-bond conjugated to ring $\pi$-bond), is ordinarily not relevant to the progress of the Diels-Alder reaction or to the effectiveness and absorption spectrum of the resulting product. $R^3$ can thus be, for example, lower alkyl (1-4 C), or $\omega$-carboxyalkyl (2-6 C) or the esters or amides thereof. The $R^3$ substituent may also be substituted with halogen as above-defined, or with other nonreactive substituents. However, as the convenient starting materials for the Gp compounds of the invention are the naturally occurring porphyrins, the preferred substituents for $R^3$ are $CH_2CH_2COOH$ or $—CH_2CH_2COOR$, wherein R is alkyl (1–6 C).

It should be noted that while the nature of the $R^3$ substituent does not ordinarily influence the course of the Diels-Alder reaction by altering the nature of the diene substrate, derivatization may be necessary to promote the reaction by providing suitable solubility characteristics or to prevent interference with the reaction. Thus, the Diels-Alder reactions described by Morgan et al and by Pangka et al utilized the dimethylester of protoporphyrin-IX as a substrate in order to prevent interference with the reaction by the free carboxyl group and to provide suitable solubility characteristics.

In the BPD compounds useful in the invention, it has been found advantageous to hydrolyze or partially hydrolyze the esterified carboxy group in $—CH_2CH_2COOR$. The hydrolysis occurs at a much faster rate than that of the ester groups of $R^1$, $R^2$, and the solubility characteristics of the resulting compounds are more desirable than those of the unhydrolyzed form. Hydrolysis results in the diacid or monoacid products (or their salts).

The green porphyrins which directly result from the Diels-Alder reaction described in the cited references can also be isomerized as therein described (see Morgan et al and Pangka et al (supra)) to compounds of formulas shown as 3 and 4 of FIG. 1 by treatment with suitable reagents such as triethylamine (TEA) in methylene chloride or 1,5-diaza bicyclo [5.4.0] undec-5-ene (DBU). The stereochemistry of the product is determined by the choice of reagent.

The depictions of compounds 3 and 4 in FIG. 1 do not show the relative position of the exocyclic methyl group (ring A of formula 3 and ring B of formula 4) with respect to the $R^2$ substituent. It has been found by these authors that rearrangement using TEA gives cis geometry for the angular methyl group and $R^2$, while treatment with DBU results in the trans product. This cis product is evidently kinetically controlled since treatment of the cis product with DBU results in a further rearrangement to trans stereochemistry. Thus, formulas 3 and 4 of FIG. 1 show the rearranged products generically, from either TEA or DBU catalyzed rearrangement in rings A and B respectively.

In addition, the Diels-Alder products can be selectively reduced by treating with hydrogen in the presence of palladium on charcoal to give the saturated ring analogs, shown as formulas 5 and 6 in FIG. 1, corresponding to the respective Diels-Alder products of rings A and B. These reduced products are less preferred embodiments, and are less useful in the method of the invention than the compounds of formulas 1–4.

The description set forth above with respect to the compounds of formulas 1 and 2 concerning derivatization by conversion of the remaining vinyl substituent ($R^4$) and with respect to variability of $—R^3$ applies as well to the compounds of formulas 3, 4, 5 and 6.

The compounds of formulas 3 and 4 (BPD), and especially those which have hydrolyzed and partially hydrolyzed carbalkoxy groups in $R^3$, are most preferred. Compounds of the invention which contain $—COOH$ may be prepared as the free acid or in the form of salts with organic or inorganic bases.

It will be noted that many of the compounds of FIG. 1 contain at least one chiral center and therefore exist as optical isomers. The compositions and methods of the invention include Gp compounds having both configurations of the chiral carbons, whether the compounds are supplied as isolates of a single stereoisomer or are mixtures of enantiomers and/or diastereomers. Separation of mixtures of diastereomers may be effected by any conventional means; mixtures of enantiomers may be separated by usual techniques of reacting them with optically active preparations and separating the resulting diastereomers.

It should further be noted that the reaction products may be unseparated mixtures of A and B ring additions, e.g., mixtures of formulas 1 and 2 or 3 and 4 or 5 and 6. Either the separated forms—i.e., formula 3 alone or 4 alone, or mixtures in any ratio may be employed in the methods and compositions set forth herein.

Figure 2:
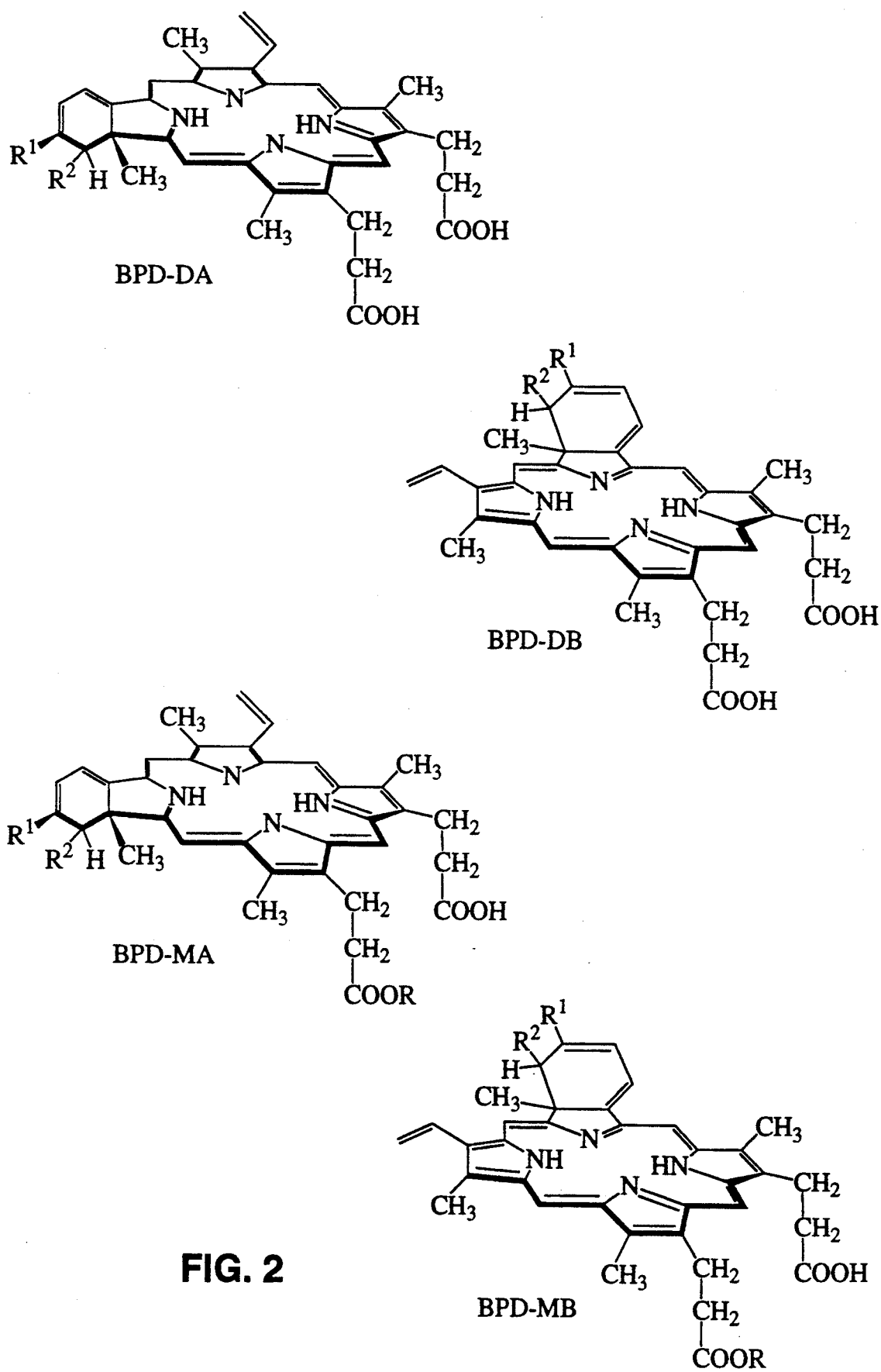
FIG. 2 shows the structure of four preferred forms of the hydro-monobenzoporphyrin derivative of formulas 3 and 4.
Figure 3:
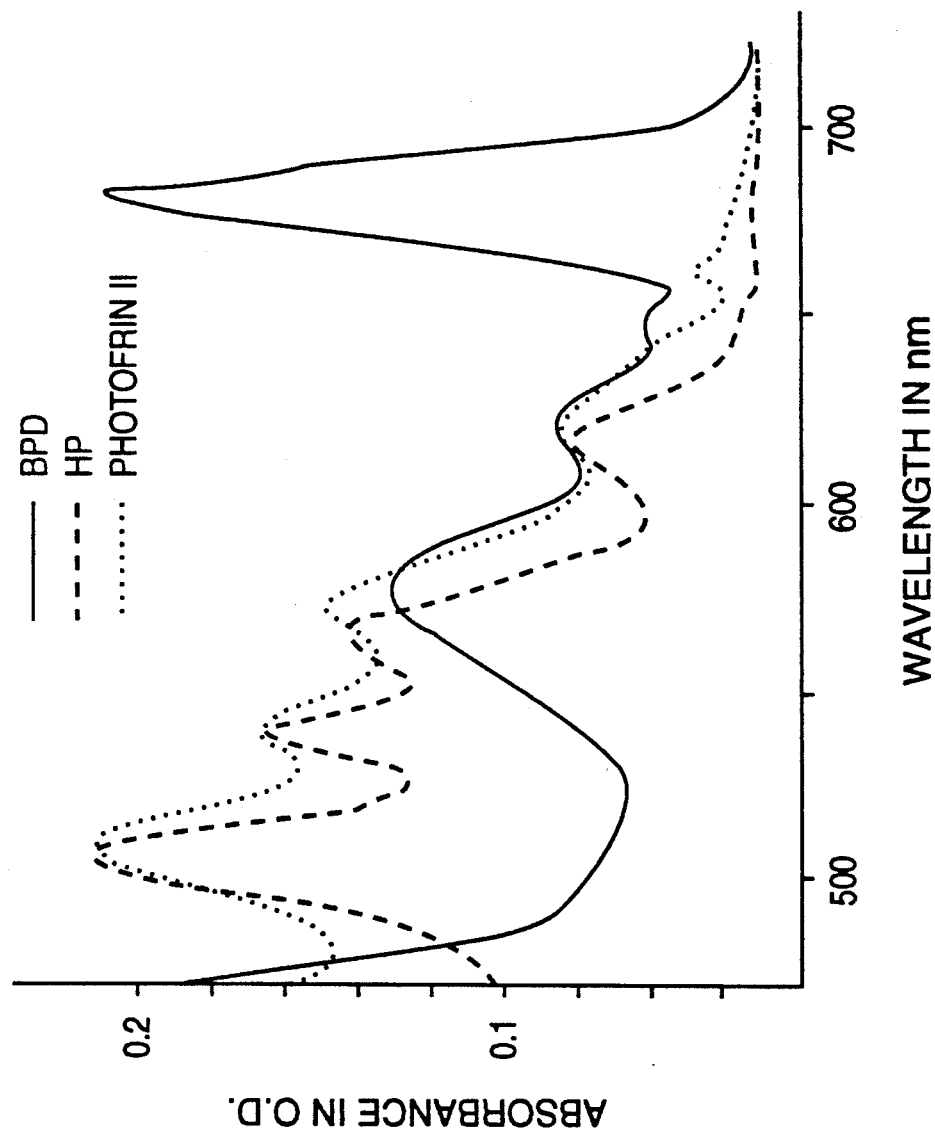
FIG. 3 shows a comparative absorption spectrum of a BPD compound and prior art compositions.

FIG. 2 shows four particularly preferred BPDs useful in the invention. These compounds are collectively designated benzoporphyrin derivative (BPD) as they are forms of Gp having the formula 3 or 4. These are hydrolyzed or partially hydrolyzed forms of the rearranged products of formula 3 and 4, wherein one or both of the protected carboxyl groups of $R^3$ are hydrolyzed. The ester groups at $R^1$ and $R^2$ hydrolyze relatively so slowly that conversion to the forms shown in FIG. 2 is easily effected.

For purposes of this description, $R^3$ is $—CH_2CH_2COOR^{3'}$. As shown in FIG. 2, each $R^3$ is H in preferred compound BPD-DA, $R^1$ and $R^2$ are carbalkoxy, and derivatization is at ring A; BPD-DB is the corresponding compound wherein derivatization is at ring B. BPD-MA represents the partially hydrolyzed form of BPD-DA, and BPD-MB, the partially hydrolyzed form of BPD-DB. Thus, in these latter compounds, $R^1$ and $R^2$ are carbalkoxy, one $R^{3'}$ is H and the other $R^{3'}$ is alkyl (1–6 C). The compounds of formulas BPD-MA and BPD-MB may be homogeneous wherein only the C ring carbalkoxyethyl or only the D ring carbalkoxyethyl is hydrolyzed, or may be mixtures of the C and D ring substituent hydrolysates. In addition, mixtures of any two or more of BPD-MA, -MB, -DA and -DB may be employed in the method of the invention.

In summary and in general, in the Gp of the invention as shown in FIG. 1, each $R^1$ and $R^2$ is independently selected from the group consisting of carbalkoxy (2–6 C), alkyl (1–6 C) sulfonyl, aryl (6–10 C) sulfonyl, aryl (6–10 C); cyano; and $—CONR^5CO—$ wherein $R^5$ is aryl (6–10 C) or alkyl (1–6 C);

each $R^3$ is independently carboxyalkyl (2–6 C) or a salt, amide, ester or acylhydrazone thereof, or is alkyl (1–6 C); and $R^4$ is $CHCH_2$, $CHOR^{4'}$, $—CHO$, $—COOR^{4'}$, $CH(OR^{4'})CH_3$, $CH(OR^{4'})CH_2OR^{4'}$, $—CH(SR^4)CH_3$, $—CH(NR^{4'}{}_2)CH_3$, $—CH(CN)CH_3$, $—CH(COOR^{4'})CH_3$, $—CH(OOCR^{4'})CH_3$, $—CH(halo)CH_3$, or $—CH(halo)CH_2(halo)$, wherein $R^{4'}$ is H, alkyl (1–6 C) optionally substituted with a hydrophilic substituent, or wherein $R^4$ is an organic group of $<12$ C resulting from direct or indirect derivatization of vinyl, or wherein $R^4$ is a group containing 1–3 tetrapyrrole-type nuclei of the formula -L-P as herein defined.

Compounds of the formulas 3 and 4 and mixtures thereof are particularly preferred. Also preferred are those wherein $R^1$ and $R^2$ are the same and are carbalkoxy, especially carboethoxy; also preferred are those wherein $R^4$ is $—CHCH_2$, $CH(OH)CH_3$ or $—CH(halo)$ CH₃, or is a group containing 1-3 tetrapyrrole-type nuclei of the formula —L—P (defined below).

As used herein, "tetrapyrrole-type nucleus" represents a four-ring system of the skeleton:

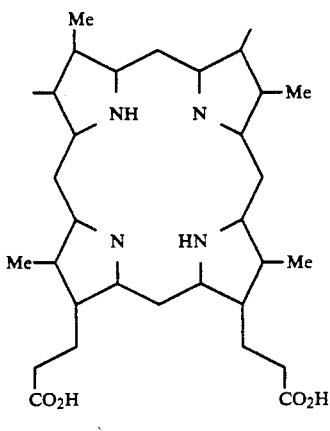

which is abbreviated

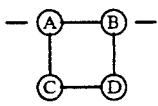

which is highly conjugated. It includes the porphyrin system, which is, in effect, a completely conjugated system, the chlorin system, which is, in effect, a dihydro form of the porphyrin, and the reduced chlorin system, which is a tetrahydro form of the completely conjugated system. When "porphyrin" is specified, the completely conjugated system is indicated; Gp is effectively a dihydro form of the porphyrin system.

When $R^4$ is —L—P, the substituent formula "—L—P" represents a substituent wherein —L— is selected the group consisting of

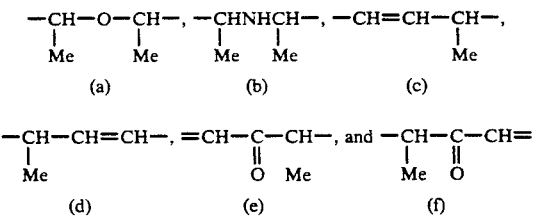

and P is a tetrapyrrole type nucleus as above-described.

(It is also understood that when —L— is of the formula (e) or (f), the ring system to which the double bond is attached will have a resonance system corresponding to

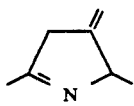

in the ring to which the double bond is attached, as shown.)

The "P" to which L is attached can, of course, include porphyrin, Gp or other tetrapyrrole-type nuclei. The Gp compounds include embodiments wherein the "P" of L—P is further thus derivatized, thus resulting in a trimer or oligomer.

In one embodiment, the lipoprotein mixtures of this invention are derived from human plasma. Preferably, the lipoprotein mixture consists essentially of lipoproteins having a specific density range, such as HDLs, LDLs or VLDLs. It may contain a reconstituted portion of previously lyophilized lipoproteins. The lipoprotein mixture may also consist of lipoproteins and phospholipids or both constituted in liposomal form.

Lipoproteins may be obtained synthetically as well. Lipoprotein segments or fragments may be used, and methods for preparing recombinant lipoproteins can also be employed. When preparing recombinant lipoproteins in a host organism, only the protein component of the lipoprotein ("apolipoprotein") will be synthesized by the host organism. The apolipoproteins are then associated with the appropriate cholesterols, triglycerides, phospholipids and serum lipids to form the lipoprotein. Apolipoprotein fragments and apolipoprotein-like polypeptides may also be synthesized recombinantly to form new lipoproteins.

The liposomal forms in this invention may employ any of the known components of phospholipid membranes, including but not limited to dipalmitoyl- or dimyristoyl-phosphatidylcholine, or phosphatidylserine, phosphatidylethanolamine, phosphatidylglycerol or sphingolmyelin analogs. They may also incorporate lipoproteins derived from human plasma as above.

The liposomes of this invention may be prepared by standard methods. Liposomes may be formed simply by suspending the appropriate lipid or lipids in an aqueous medium. The solution is then sonicated to yield a uniform dispersion of multilamellar liposomes, which may then be broken up mechanically to obtain unilamellar liposomes. Liposomes may also be prepared by mixing a solution of lipids in ethanol with water. Alternatively, liposomes may be formed from lipids at the phase transition between an organic layer and an aqueous layer.

In one preferred embodiment, the Gp is either BPD-MA or BPD-DA, and the lipoprotein mixture comprises either HDLs, LDLs, VLDLs or a combination thereof. In a particularly preferred embodiment, the composition comprises BPD-MA and HDLs.

Additional Components

Although the compositions of this invention comprise two main components, it should be understood that in addition to the green porphyrin and lipocomplex, certain additional components may be coupled to a component of the composition. These include targeting components, additional label, and other functionalities which may be useful in the applications herein.

For example, an immunoglobulin or portion thereof or a ligand specific for receptor can be used as a target specific component. The immunoglobulin can be polyclonal or monoclonal antibody and may comprise whole antibodies or immunologically reactive fragments of these antibodies such as F(ab')₂, Fab, or Fab' fragments. Use of such immunologically reactive fragments as substitutes for whole antibodies is well known in the art. See, for example, Spiegelberg, H. L., in "Immunoassays in the Clinical Laboratory" (1978) 3:1-23.

The ligand specific for receptor will be a moiety which binds a receptor at cell surfaces, and thus contains contours and charge patterns which are complementary to those of the receptor. A variety of cell types have specific receptors designed to bind hormones, growth factors, or neurotransmitters, and these ligands specific for receptor are included as well as synthetic materials which bind specifically to a receptor. Examples of such ligands include the steroid hormones, such as progesterone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth: and neurotransmitters, such as acetylcholine, serotonin, and dopamine, as well as analogs of these substances which bind receptors.

The compositions of the invention may contain components derivatized to a compound or ion which is a label. A wide variety of labeling moieties can be used, including radioisotopes, chromophores, and fluorescent labels. Radioisotope labeling in particular can be readily detected in vivo. Radioisotopes may be coupled by coordination as cations in the porphyrin system. Useful cations include technetium, gallium, and indium. In the compositions, either the porphyrin or the lipophilic component can be linked to or associated with label.

In general, the compositions can also be administered or used in in vitro methods when complexed to appropriate metal ions. As is generally understood in the art, the tetrapyrrole-type nucleus can be treated with an appropriate ion such as magnesium ion, zinc ion, stannous ion, and the like to obtain the metal complex. As stated above, the metal ion may also be a radiolabel. The nature and desirability of the inclusion of a metal ion in the tetrapyrrole-type nucleus depends on the specific application for which the conjugate is intended. When the inclusion of a metal ion is desired, the desired metal ion can be inserted using the appropriate metal salts under known conditions. For example, zinc ion can be introduced by treating the compound with zinc acetate in 1:1 methylene chloride:methanol.

Preparation

The Gp and the lipocomplex are preferably preincubated together prior to their administration. The preincubation may be performed at temperatures between 20° C. and 40° C. for a period which may range from about 10 minutes up to several hours, more preferably about 30 to 60 minutes.

When the lipocomplex is a liposome, the Gp-liposome preparation may proceed as above, or the Gp may be incorporated in the aqueous compartment of the interior of the liposome. This is achieved by the common technique of forming the liposomes in the presence of Gp.

The preincubation of the two components is performed preferably at ratios in a range from 10-fold weight/weight excess of lipocomplex to Gp, up to 100-fold weight/weight excess of Gp to lipocomplex, more preferably 5-fold to 20-fold weight/weight excess of Gp. Of course, the overriding factor determining this ratio is that ratio which optimally and preferentially delivers the lipocomplex-associated Gp to tumor cells. This "optimal ratio" can be ascertained readily for various Gps and lipocomplexes by routine experimentation.

Administration and use

The combinations of this invention are formulated into pharmaceutical compositions for administration to the subject using techniques known in the art generally. A summary of such pharmaceutical compositions may be found, for example, in *Remington's Pharmaceutical Sciences*, Mack Publishing Co., Easton, Pa., latest edition.

The combinations of the present invention are normally administered systemically, preferably by injection. Injection may be intravenous, subcutaneous, intramuscular or intraperitoneal. Injectables can be prepared in conventional forms, either as liquid solutions or suspensions, solid form suitable for solution or suspension in liquid prior to injection, or as emulsions. Suitable carrier solutions are, for example, water, saline, dextrose, glycerol and the like. Of course, these compositions may also contain minor amounts of nontoxic, auxiliary substances such as wetting or emulsifying agents, pH buffering agents and so forth.

If the treatment is to be localized, such as for the treatment of superficial tumors or skin disorders, the active combinations may be topically administered using standard topical compositions involving lotions, suspensions, or pastes.

The quantity of combination and ratio therein to be administered depends on the choice of active ingredients, the condition to be treated, the mode of administration, the individual subject, and the judgment of the practitioner. Depending on the specificity of the combination, smaller or larger doses may be needed. For those combinations with the highest affinity for tumor tissue, such as BPD-MA in conjunction with LDLs, dosages in the range of less than 1 mg/kg are suggested. For less specific combinations, dosages up to 10 mg/kg may be needed. These ranges are merely suggestive, as the number of variables which will determine a particular treatment regime is large and considerable excursions from these recommended values are expected.

For co-injection in cancer patients, the two active components are added to a pharmaceutically acceptable injectable carrier solution. This solution will typically be buffered at a physiological pH (about 7.4), and may contain other components that do not interact with the lipocomplex-associated Gp such as inorganic salts, simple carbohydrates and the like.

In the methods of this invention, injection of the lipocomplex-associated Gp is followed by light irradiation. Preferably there will be a waiting period between injection and irradiation. This waiting period may range from less than one hour to about 24 hours or more. More preferably, the wait will be between about two and six hours. Decisive factors in this determination will be the type of lipocomplex used, and the halflife of the composition in normal tissue. LDLs have a shorter half-life in terms of their ability to maintain the Gp-tumor cell association. For LDLs, then, the most preferable waiting time would be about two to three hours. HDLs have a much stronger ability to maintain the Gp-cell association and therefore the waiting time may be extended to about eight hours or more.

The wavelength of irradiating light is preferably chosen to match the maximum absorbance of the Gp. A Gp, including a BPD, may be excited by light in the 400–750 nm range. For BPD-MA and BPD-DA, the preferable wavelength is between about 680 and 700 nm. Preferred irradiation dosages are in the range of 50–500 J cm$^{-2}$, and preferred irradiation dosage rates are in the range of 100–300 mW cm$^{-2}$.

The following example is intended to illustrate the invention but not to limit its scope.

EXAMPLE 1

The method to prepare the compositions of this invention involves: (1) synthesis of a Gp photosensitizer; (2) isolation of a lipoprotein mixture; and (3) incubation of these two components prior to co-injection. In this example, BPD-MA and HDLs are used.

(a) Synthesis of Benzoporphyrins. Synthesis of benzoporphyrins was performed according to the method of Richter, A. M. et al., *J. Natl. Cancer Inst.* 79:1327–1332 (1987). BPD-MA (the monoacid derivative) was purified from BPD-DA (the diacids) by silica gel column chromatography.

BPD-MA was labeled with tritium (New England Nuclear (NEN)). Purity of the $^3$H-BPD products was determined by thin-layer chromatography (TLC) and biological activity measured by a standard cytotoxicity assay as in Richter, A. M. et al., supra. The specific activity of $^3$H-BPD-MA used was 5.46–5.9 mCi/mg.

$^{14}$C-BPD-MA was synthesized by the method of Richter, A. M. et al., *J. Photochem. Photobiol.* 50 (in print 1990), except that Protoporphyrin IX was reacted with 2,3-$^{14}$C-dimethylacetylene-dicarboxylate (specific activity 44.0 mCi/mM) which resulted in the incorporation of $^{14}$C into the cyclohexadiene ring of the BPD-MA product. The specific activity of the $^{14}$C-BPD-MA was 60.8 µCi/mg and its purity was determined by TLC. BPD-MA was stored in dimethylsulfoxide (DMSO) at −70° C. at a concentration of 8 mg/ml and diluted immediately before use.

(b) Determining BPD Plasma Distribution. Experiments were performed to determine the association of BPDs with plasma protein and lipoprotein fractions. When density ultracentrifugation was used for the analysis, 2 ml samples of human plasma were incubated for 18 hours at 4° C. in the presence of 100 µg of $^3$H-BPD-MA. The BPD-plasma solution was then adjusted to a density of 1.21 g/ml by the addition of solid KBr. A step gradient was prepared using stock KBr density solutions at 1.006, 1.019, and 1.063 g/ml, layered manually into the bottom of centrifuge tubes using a glass syringe and a narrow bore needle. The BPD-plasma solution was then layered into the bottom of the tube. Separation of the plasma proteins was accomplished by centrifugation in a Beckman SW 41 rotor for 24 hours at 40,000 rpm and 15° C. 0.5 ml fractions were collected, and the protein content of each fraction was monitored by measuring absorbance at 280 nm. 100 µl of each fraction was mixed with 5 ml Aquasol (NEN) and counted in a liquid scintillation counter.

In the alternative, chromatography was also used for the analysis. The BPD-plasma solution was applied to a Biogel A 5.0 M chromatographic column (90 cm ×1.5 cm) and eluted with 0.15 M NaCl, 10 mM Tris-HCl, 0.01% EDTA, 0.05% NaN$_3$, pH 7.4 at 10 ml/h. The eluate was collected from the column in 2.5 ml fractions. Each fraction was assayed for protein content by measuring absorbance at 280 nm. $^3$H-BPD-MA as assessed by diluting 100 µl of each fraction in 5 ml Aquasol (NEN) before counting in a Packard Tri-Carb 4550 liquid scintillation counter. Calibration of the column with human $^{125}$I-VLDL, -LDL, and -HDL allowed for identification of the resulting peaks.

Figure 4:
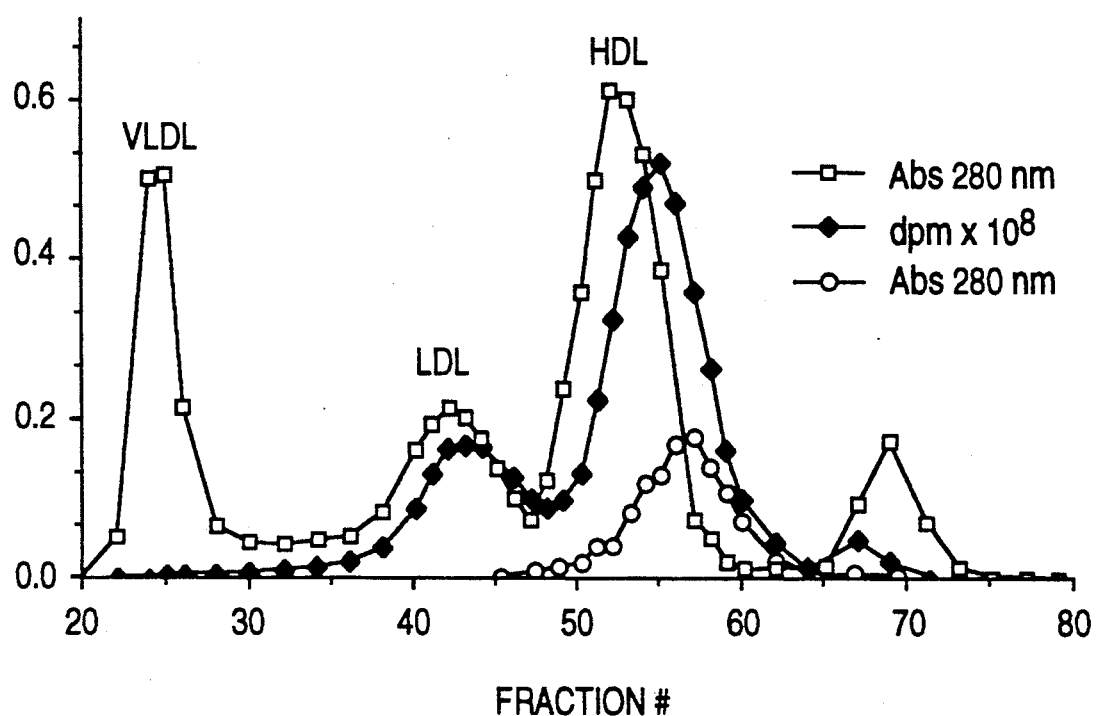
FIG. 4 shows the elution profile of $^3$H-BPD-MA mixed with human plasma from a Biogel A5.0 M column. The closed diamonds show the profile of the BPD relative to the lipoproteins and albumin.

The elution profile of $^3$H-BPD-MA, presented in FIG. 4, demonstrates the resolution of the three main lipoprotein classes. The profile indicated that the majority of $^3$H-BPD-MA eluted with HDL and albumin. A lesser amount eluted with LDL, and a small amount with other plasma proteins eluting after the HDL peak. VLDL bound almost no $^3$H-BPD-MA. Poor resolution of HDL from albumin suggested that albumin binding might contribute to the apparent HDL binding.

To improve the HDL-albumin resolution, albumin was removed by ultracentrifugation. Plasma was mixed with $^{14}$C-BPD-MA and incubated for 18 hours at 4° C. The density of the mixture was then adjusted to 1.21 g/ml by the addition of solid KBr, followed by centrifugation at 40,000 rpm for 48 hours. This resulted in the separation of the lipoproteins from other plasma proteins. The lipoprotein and lipoprotein-depleted fractions were counted for BPD-MA content. 82% of total $^{14}$C-BPD-MA added was recovered in the plasma lipoprotein fraction and 5% in the lipoprotein deficient fraction.

Figure 5:
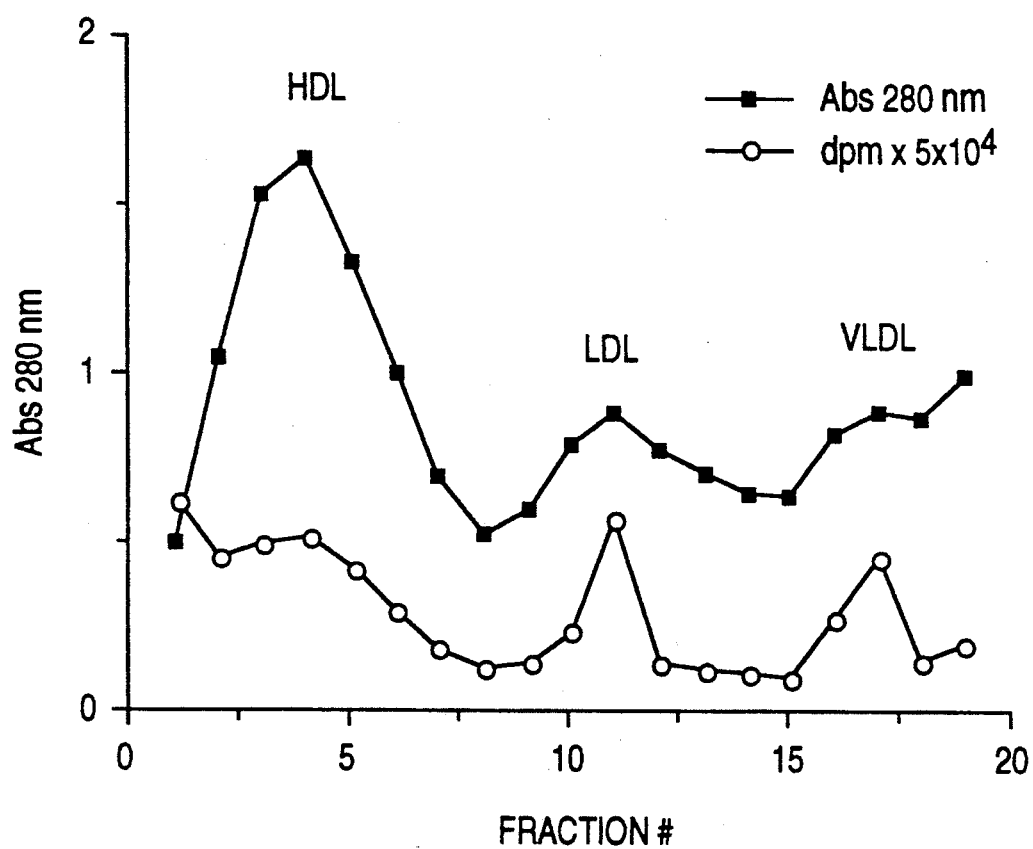
FIG. 5 shows the density gradient of $^{14}$C-BPD-MA in the plasma lipoprotein fraction of human plasma. The open squares show the distribution of lipoproteins, and the closed diamonds show the relative distribution of the labelled BPD.
Figure 6:
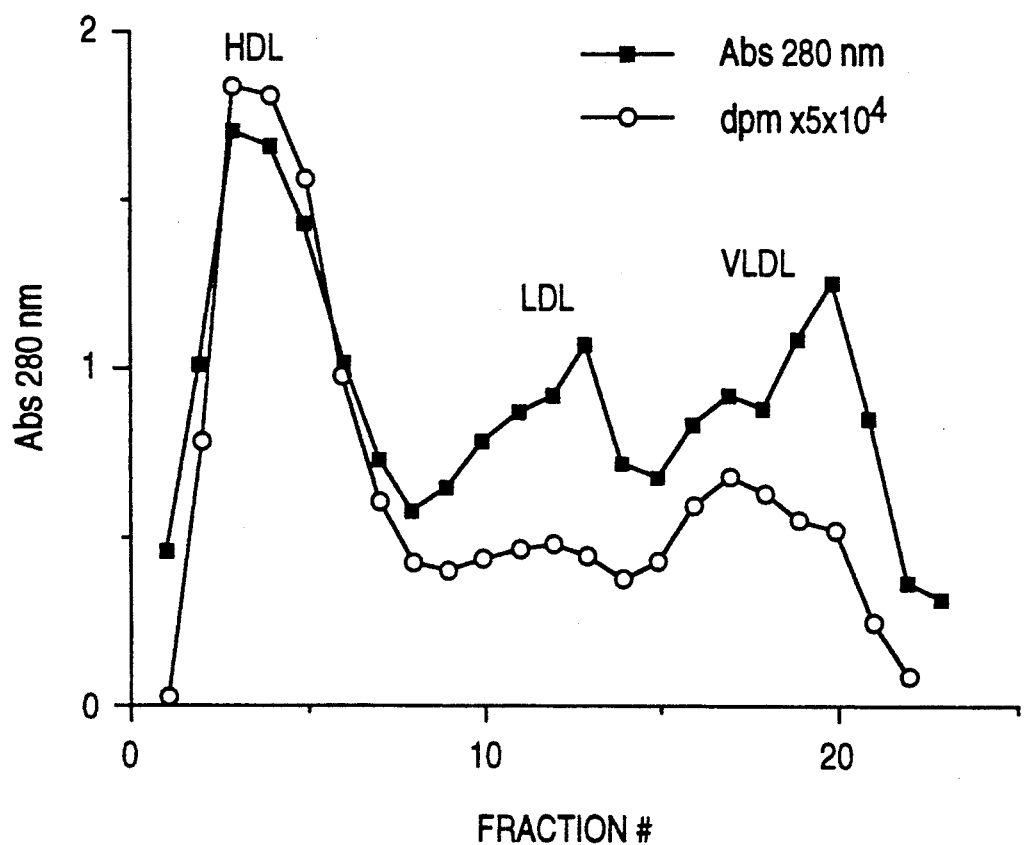
FIG. 6 shows the density gradient of $^{14}$C-BPD-DA in the plasma lipoprotein fraction of human plasma, as in FIG. 5.

When albumin and other serum proteins were separated from the lipoprotein fraction before the addition of $^{14}$C-BPD-MA, a shift in binding was observed. After step density gradient separation, the majority of BPD-MA was still recovered with HDL (38% of total $^{14}$C-BPD-MA added); however in this case, the association with LDL and VLDL fractions appeared to be equivalent (17% with LDL and 18% with VLDL) (FIG. 5). Similar studies with BPD-DA added to the lipoprotein fraction indicated that a higher percentage associated with HDL (54%) and VLDL bound slightly more than LDL (20% and 13% respectively) (FIG. 6). Polyacrylamide gel electrophoresis of the HDL fractions from these density gradients confirmed that very little albumin was present. Thus, the association of BPD-MA and BPD-DA with HDL was not due to albumin contamination. Similar results were obtained in these experiments with both $^3$H-BPD-MA and $^{14}$C-BPD-MA.

(c) Preparation of Plasma Lipoproteins. Lipoprotein fractions were isolated from fresh human plasma by preparative ultracentrifugation. Three fractions (HDLs, LDLs, VLDLs) were recovered by sequential flotation, according to Havel, R. J. et al., *J. Clin. Invest.* 34:1345–1353 (1955). The purity of each fraction was determined by agarose gel electrophoresis. The total lipoprotein concentration was estimated by analysis of protein content.

(d) Preparation of Injection. The compositions were prepared for injection into mature DBA2J mice bearing the M1 tumor (DBA/2 methylcholanthrene induced rhabdomyosarcoma). Prior to injection, the two active components are preincubated together. 80 µg $^3$H-BPD-MA was provided in 0.1 ml Tris:EDTA buffer (0.15 M NaCl, 10 mM Tris:HCl, 0.01% EDTA, 0.05% NaN3, pH 7.4) containing 10% DMSO. When using $^{14}$C-BPD-MA, each mouse received 100 µg BPD in similar solutions. HDL and VLDL were used at 1 mg/ml and 0.1 mg/ml (in 10% DMSO) respectively with both $^{14}$C-BPD-MA and $^3$H-BPD-MA. LDL was used at 2 mg/ml in experiments with both isotopes. Since the total volume provided was 0.1 ml, the weight/weight ratio of BPD to lipoprotein ranged from a low of 2:5 ($^3$H-BPD-MA and LDL) up to 10:1 ($^{14}$C-BPD-MA and VLDL). $^3$H-BPD-MA or $^{14}$C-BPD-MA was incubated with the lipoprotein fraction for 30 min at 37° C.

(e) Biodistribution of BPD in Tumor-bearing Mice. Following preincubation, the compositions were ready for co-injection. Tumor-bearing mice were injected with one of the lipoprotein-BPD mixtures described above. At 3, 8, or 24 hours post-injection mice were sacrificed by cervical dislocation under light ether anaesthesia and samples of blood, brain, heart, intestine, kidney, liver, muscle, skin, spleen, lymph node, feces, urine, bone marrow, and tumor tissue were excised. Sample were placed in 7 ml vials, minced, and the wet weight or volume was determined. In addition the total wet weight of each tumor was determined before duplicate samples were prepared for counting.

Samples were processed by solubilization in 1 ml Protosol (NEN) for 3 days at 50° C. The solubilized samples were bleached with 100 μl of 30% $H_2O_2$ and mixed with 5 ml of Econofluor (NEN). After 3 to 4 hours adaptation in the dark, samples were counted in a Packard Tri-Carb 4550 liquid scinitillation counter. Counts were subsequently converted to micrograms (μg) of $^3$H-BPD-MA or $^{14}$C-BPD-MA per mg tissue.

Figure 7:
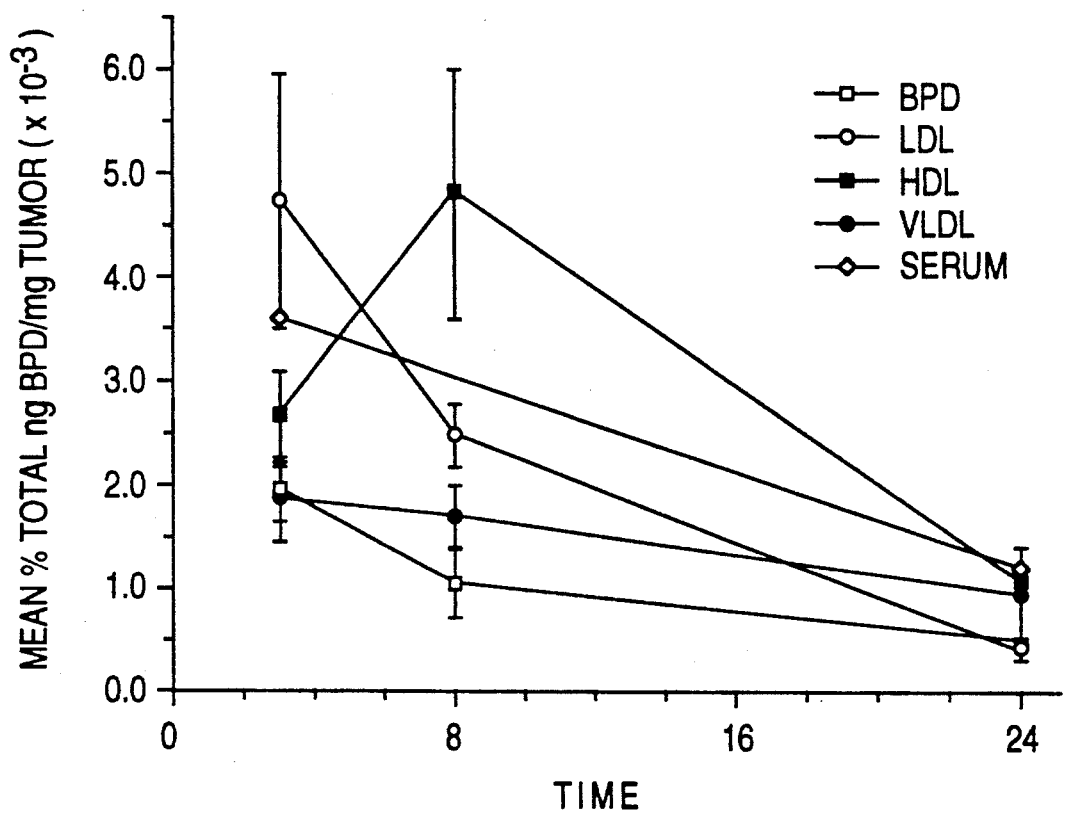
FIG. 7 shows the accumulation over time of $^3$H-BPD-MA in tumor tissue. The BPD was either injected alone (open squares) or precomplexed with serum or lipoprotein fractions as denoted.

Results of these experiments are shown in FIG. 7. At 3 hours, precomplexing BPD-MA with LDL led to a significantly ($p<0.05$) greater tumor deposition than BPD administration alone in aqueous solution. By 8 hours, the amount of BPD-MA in the tumor was decreased in most treatment cases; however the HDL mixture still resulted in enhanced deposition ($p<0.05$). By 24 hours, clearance from the tumor had taken place with all three lipoprotein mixtures as well as BPD in aqueous solution. As expected, the serum control led to accumulation in the tumor which was roughly an average of the three isolated lipoproteins.

Figure 8:
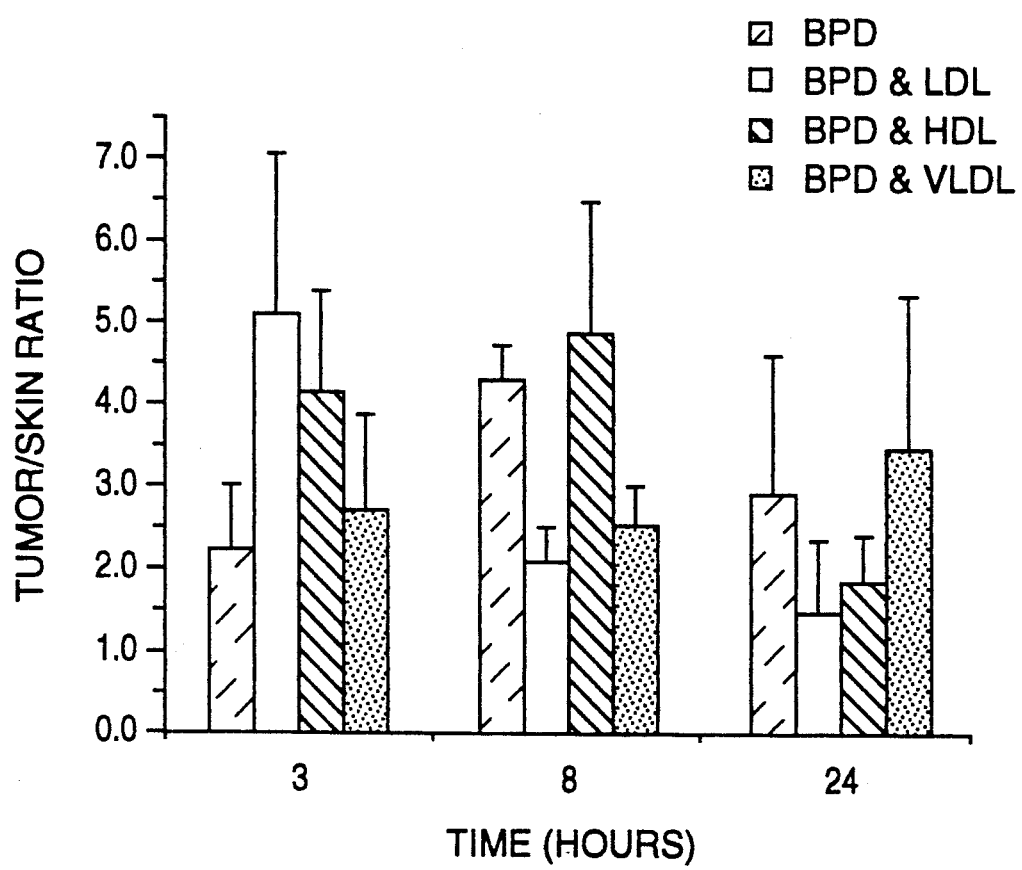
FIG. 8 shows the ratios over time of $^3$H-BPD-MA deposited in tumor tissue to that deposited in the skin. BPD was either injected alone or precomplexed with the various lipoprotein fractions.

The ratios of the mean percentage of administered BPD deposited in the tumor to that deposited in the skin are shown in FIG. 8. At 3 hours, the tumor:skin ratio for BPD in aqueous solution was consistently between 2:1 and 3:1. At this point, precomplexing with both LDL and HDL led to significantly higher tumor to skin ratios (5.1:1 and 4.1:1, respectively). By 8 hours, this ratio was still increased with HDL (4.9:1), but the effect was no longer observed with LDL. After 24 hours, the lipoprotein mixtures showed no advantage over BFD-MA in aqueous solution, with respect to tumor to skin ratio.

The mean percentage of total $^{14}$C-BPD-MA administered which was found to accumulate in various tissues are presented in Tables 1 and 2. At all time points, accumulation was highest in the liver, kidney and spleen and lowest in bone marrow and brain. Association of BPD-MA with any of the three lipoproteins led to a higher blood level at 3 and 8 hours than BPD alone. (Tables 1 and 2). By 8 hours this higher circulating level of BPD-MA was reflected in slightly higher deposition in most tissues in the presence of the lipoproteins.

In all treatment cases, tissue-associated radioactivity declined slowly with time. When BPD was delivered in aqueous solution, elimination in the urine was approximately ten times greater at 3 hours than at 8 hours. Conversely, in the presence of lipoproteins, elimination of BPD in the urine at 3 hours was lower than that at eight hours. Clearance in the feces was higher when BPD was delivered precomplexed with lipoproteins rather than in aqueous solution.

TABLE 1

| $^{14}$C-BPD-MA Tissue | Biodistribution Results at 3 hours | | | |
|---|---|---|---|---|
| | BPD | BPD & LDL | BPD & HDL | BPD & VLDL |
| Blood | 2.34 ± 0.12 | 4.42 ± 0.43 | 2.69 ± 0.38 | 4.35 ± 1.40 |
| Brain | 0.66 ± 0.02 | 0.53 ± 0.06 | 0.26 ± 0.04 | 1.66 ± 1.87 |
| Heart | 2.34 ± 0.01 | 3.67 ± 0.24 | 2.66 ± 0.63 | 8.02 ± 8.93 |
| Intestine | 3.35 ± 2.87 | 7.64 ± 2.69 | 2.49 ± 0.56 | 2.41 ± 0.12 |
| Kidney | 3.92 ± 0.17 | 11.22 ± 7.35 | 3.05 ± 2.29 | 16.12 ± 19.48 |
| Liver | 25.27 ± 1.57 | 21.90 ± 4.89 | 11.58 ± 8.08 | 25.73 ± 21.15 |
| Muscle | 2.50 ± 2.16 | 3.89 ± 3.79 | 0.70 ± 0.18 | 1.06 ± 0.31 |
| Spleen | 10.37 ± 3.46 | 21.46 ± 3.95 | 6.16 ± 1.27 | 15.33 ± 4.53 |
| Lymph Node | 1.95 ± 1.52 | 18.58 ± 20.52 | 4.26 ± 4.46 | 4.94 ± 2.21 |
| Feces | 2.39* | 42.27 ± 32.14 | 17.43 ± 8.80 | 59.18 ± 69.6 |
| Urine | 551.84 ± 310.40 | 147.92 ± 58.56 | 109.68 ± 94.80 | 267.04 ± 184.08 |
| Gall Bladder | 12.25 ± 9.15 | 303.84 ± 446.58 | 26.06 ± 10.00 | 26.89 ± 4.82 |
| Bone Marrow | 0.01 ± 0.00 | 0.12 ± 0.07 | 0.01 ± 0.00 | 0.19 ± 0.19 |
| Tumor | 2.70 ± 2.12 | 13.36 ± 6.55 | 2.38 ± 1.14 | 5.66 ± 2.54 |
| Skin | 1.61 ± 1.08 | 1.10 ± 0.22 | 0.78 ± 0.42 | 2.02 ± 0.99 |

Values represent BPD accumulated in tissue expressed as mean percent of total BPD administered × $10^{-3}$
*one sample only

TABLE 2

| $^{14}$C-BPD-MA Tissue | Biodistribution Results at 8 hours | | | |
|---|---|---|---|---|
| | BPD | BPD & LDL | BPD & HDL | BPD & VLDL |
| Blood | 1.26 ± 0.07 | 5.09 ± 5.90 | 2.33 ± 0.07 | 2.42 ± 0.76 |
| Brain | 0.55 ± 0.23 | 0.43 ± 0.23 | 1.15 ± 0.82 | 0.30 ± 0.08 |
| Heart | 1.97 ± 0.82 | 1.04 ± 0.17 | 1.81 ± 0.46 | 1.30 ± 0.39 |
| Intestine | 0.96 ± 0.18 | 1.18 ± 0.53 | 1.37 ± 0.17 | 1.53 ± 0.41 |
| Kidney | 2.31 ± 0.19 | 2.40 ± 0.75 | 6.49 ± 6.07 | 3.07 ± 0.70 |
| Liver | 17.49 ± 1.52 | 9.39 ± 1.42 | 11.97 ± 0.52 | 24.50 ± 6.22 |
| Muscle | 0.55 ± 0.17 | 0.78 ± 0.31 | 0.45 ± 0.03 | 0.42 ± 0.08 |
| Spleen | 8.90 ± 4.16 | 6.42 ± 1.74 | 5.23 ± 1.32 | 10.22 ± 5.40 |
| Lymph Node | 0.77 ± 0.35 | 3.91 ± 2.04 | 2.54 ± 0.94 | 1.68 ± 0.22 |
| Feces | 50.67 ± 69.29 | 122.24 ± 145.04 | 274.48 ± 117.76 | 297.36 ± 214.80 |
| Urine | 50.00 ± 2.55 | 719.52 ± 370.72 | 720.40 ± 157.28 | 111.12 ± 55.92 |
| Gall Bladder | 2.43 ± 0.52 | 22.21 ± 13.02 | 7.33 ± 6.14 | 11.63 ± 8.19 |
| Bone Marrow | 0.28 ± 0.43 | 0.15 ± 0.21 | 0.00 ± 0.00 | 0.01 ± 0.00 |
| Tumor | 1.49 ± 0.29 | 3.50 ± 1.02 | 2.54 ± 0.53 | 2.77 ± 0.52 |
| Skin | 0.47 ± 0.17 | 1.23 ± 0.12 | 1.21 ± 0.69 | 1.37 ± 0.58 |

Values represent BPD accumulated in tissue as mean percent of total BPD administered × $10^{-3}$ (f) Irradiation Treatment. For methods of irradiation treatment following composition administration, see Dougherty, T. J. et al., in "Porphyrin Photosensitization," D. Kessel et al., eds., pp. 3–13 (1983: Plenum Press).

Patients requiring radiation treatment are injected intravenously with a solution containing a BPD and HDLs in a 1:1 ratio (w/w) at a dosage of 4 mg BPD/kg body weight. The solution is allowed to be metabolized in the body for 24 hours. Subsequent to this waiting period, the patient is exposed to a tunable dye laser composed of quartz fibers at a wavelength of 690 nm. The laser may be introduced to the tumor through the skin, or directly to the tumor via needle, or using esophagoscopes, bronchoscopes, cystoscopes or catheters if necessary. The patient receives a dosage of about 100 J cm$^{-2}$. The irradiation may be repeated up to seven days following BPD injection.

(g) Irraditation Diagnosis. For methods of irradiation diagnosis following composition administration, see Kato, H. et al., *Lasers in Surgery and Medicine* 4:49–58 (1984) and Gregorie, H. B. et al., *Annals of Surgery* 167:820–828 (1968).

Patients requiring diagnoses are injected intravenously with a solution containing a BPD and HDLs in a 1:1 ratio (w/w) at a dosage of 4 mg BPD/kg body weight. The solution is allowed to be metabolized in the body for 24 hours. Subsequent to this waiting period, the patient is exposed to the diagnostic system described in Kato, H. et al., supra, consisting of a light source, endoscope system, and spectrophotometer. A laser emitting at around 690 nm is used as an excitation light source, and a white light source is used for endoscopic observation. Both sources are alternately transmitted through quartz fibers for continuous fluorescence monitoring and visual observation. The fibers are introduced at the locations where tumors are suspected, and BPD-specific fluorescence is monitored and analyzed spectrophotometrically.

We claim:

1. A pharmaceutical composition for photodynamic therapy comprising:

a green porphyrin compound having a formula selected from the group consisting of

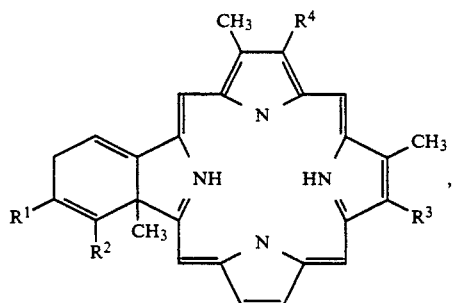

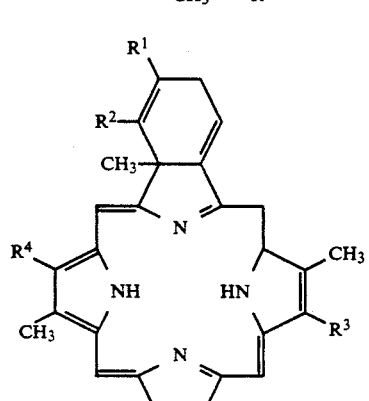

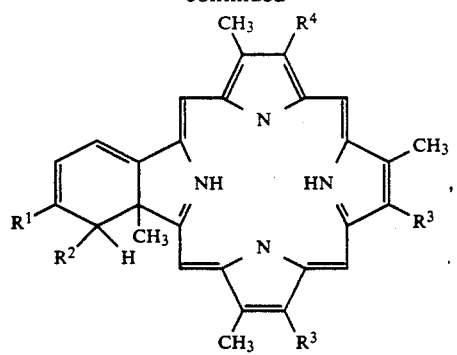

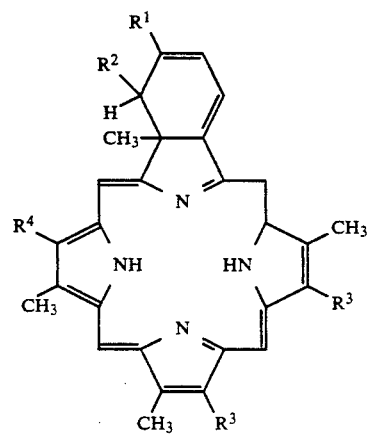

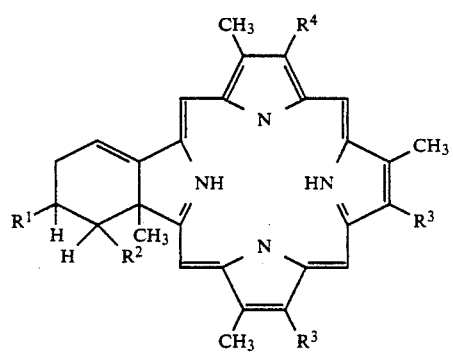 and

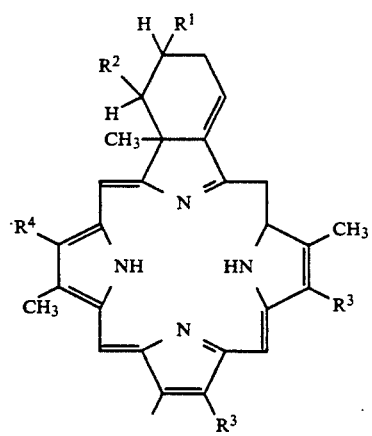

wherein
$R^1$ and $R^2$ are independently selected from the group consisting of hydrogen, carbalkoxy (2–6 C), alkyl (1–6 C) sulfonyl, aryl (6–10 C) sulfonyl, aryl (6–10

C), and cyano, further wherein at least one of $R^1$ and $R^2$ is not hydrogen;

each $R^3$ is independently selected from the group consisting of alkyl (1–6 C), carboxyalkyl (2–6 C) and salts and esters thereof; and $R^4$ is selected from the group consisting of —CH=CH$_2$, —CH$_2$OR', —CHO, —COOR', —CH(OR')CH$_3$, —CH(OR')CH$_2$OR', —CH(SR')CH$_3$, —CH(NR'$_2$)CH$_3$, —CH(CN)CH$_3$, —CH(COOR')CH$_3$, —CH(OOCR')CH$_3$, —CH(halo)CH$_3$, and —CH(halo)CH$_2$(halo), wherein each R' is hydrogen or alkyl (1–6 C);

a lipocomplex; and a pharmaceutically acceptable injectable carrier solution.

2. A composition of claim 1 wherein the green porphyrin is BPD-DA.

3. A composition of claim 1 wherein the green porphyrin is BPD-MA.

4. A composition of claim 1 wherein the lipocomplex is a lipoprotein mixture including HDL's, LDL's, VLDL's or combinations thereof.

5. The composition of claim 4 wherein the lipoprotein mixture consists essentially of HDL's.

6. The composition of claim 4 wherein the lipoprotein mixture consists essentially of LDL's.

* * * * *